(12) United States Patent
Heller et al.

(10) Patent No.: US 9,410,172 B2
(45) Date of Patent: Aug. 9, 2016

(54) ISOTHERMAL AMPLIFICATION USING OLIGOCATION-CONJUGATED PRIMER SEQUENCES

(71) Applicant: General Electric Company, Schenectady, NY (US)

(72) Inventors: Ryan Charles Heller, Guilderland, NY (US); John Richard Nelson, Clifton Park, NY (US)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 197 days.

(21) Appl. No.: 14/027,947

(22) Filed: Sep. 16, 2013

(65) Prior Publication Data

US 2015/0079635 A1    Mar. 19, 2015

(51) Int. Cl.
*C12Q 1/68* (2006.01)
*C12P 19/34* (2006.01)

(52) U.S. Cl.
CPC ............... *C12P 19/34* (2013.01); *C12Q 1/6853* (2013.01); *C12Q 1/6865* (2013.01)

(58) Field of Classification Search
None
See application file for complete search history.

(56) References Cited

U.S. PATENT DOCUMENTS

| | | | |
|---|---|---|---|
| 5,874,555 A | 2/1999 | Dervan et al. | |
| 6,017,700 A | 1/2000 | Horn et al. | |
| 6,403,302 B1 | 6/2002 | Dervan et al. | |
| 6,686,152 B2 | 2/2004 | Singh et al. | |
| 7,993,839 B2 * | 8/2011 | Nelson ................ | C12Q 1/6848 435/6.12 |
| 8,048,998 B2 | 11/2011 | Rasmussen et al. | |
| 8,067,162 B2 | 11/2011 | Hayashizaki et al. | |
| 8,465,950 B2 | 6/2013 | Kurn et al. | |
| 2003/0100113 A1 | 5/2003 | Behr et al. | |
| 2003/0118998 A1 | 6/2003 | Dean et al. | |
| 2004/0048300 A1 | 3/2004 | Sood et al. | |
| 2005/0032068 A1 | 2/2005 | Prakash et al. | |
| 2009/0069262 A1 | 3/2009 | Behr et al. | |
| 2010/0311056 A1 | 12/2010 | Lenne et al. | |
| 2011/0123520 A1 | 5/2011 | Manoharan et al. | |
| 2011/0224105 A1 | 9/2011 | Kurn et al. | |
| 2012/0190587 A1 | 7/2012 | Kurn et al. | |

FOREIGN PATENT DOCUMENTS

| | | |
|---|---|---|
| EP | 989185 B1 | 6/2004 |
| EP | 1431303 A2 | 6/2004 |
| EP | 2075342 A1 | 7/2009 |
| WO | 2012109157 A2 | 8/2012 |
| WO | 2012151560 A2 | 11/2012 |

OTHER PUBLICATIONS

Sund et al., "The Chemistry of C-Branched Spermine Tethered Oligo-Dna and Their Properties in Forming Duplexes and Triplexes", Nucleosides and Nucleotides, pp. 755-760, vol. 16, Issue 5-6, 1997.
"Zna™ A Modified Oligonucleotide", Sigma-Aldrich, 2012, pp. 1-4.
Modrusan et al., "Spermine-mediated improvement of cycling probe reaction", Molecular Cell Probes; Abstract—2 pages.
He et al., "Selective and Homogeneous Fluorescent DNA Detection by Target-Induced Strand Displacement Using Cationic Conjugated Polyelectrolytes", Analytical Chemistry, pp. 2239-2243, vol. 80, 2008.
Moreau et al., "Zip Nucleic Acids: new high affinity oligonucleotides as potent primers for PCR and reverse transcription", Nucleic Acid Research, pp. 0139, vol. 37, Issue 19, 2009.
Kwoh et al., "Transcription-Based Amplification System and Detection of Amplified Human Immunodeficiency Virus Type 1 with a Bead-Based Sandwich Hybridization Format", Proceedings of the National Academy of Sciences USA, vol. 86, No. 4, pp. 1173-1177, Feb. 1, 1989.
Noir et al., "Oligonucleotide-Oligospermine Conjugates (Zip Nucleic Acids): A Convenient Means of Finely Tuning Hybridization Temperatures", Journal of the American Chemical Society, vol. 130, No. 40, pp. 13500-13505, Oct. 8, 2008.
Tuiskunen et al., "Self-Priming of Reverse Transcriptase Impairs Strand-Specific Detection of Dengue Virus RNA", Journal of General Virology, vol. 91, No. 4, pp. 1019-1027, Nov. 25, 2009.
Turner, "Spermine Phosphoramidite: a Potent Modification with Many Applications", The Glen Report, vol. 24, No. 1, pp. 1-4, May 1, 2012.
New England Biolabs Inc., "DNA Polymerase Selection Chart", XP055155798, Nov. 28, 2014.
PCT Search Report and Written Opinion issued in connection with corresponding Application No. PCT/US2014/054944 on Dec. 8, 2014.
Harrison, et al., "Synthesis and hybridization analysis of a small library of peptide-oligonucleotide conjugates", Oxford University Press, Nucleic Acids Research, 1998, vol. 26, No. 13, pp. 3136-3145.

* cited by examiner

*Primary Examiner* — David Thomas
(74) *Attorney, Agent, or Firm* — Fletcher Yoder, P.C.

(57) ABSTRACT

Provided herein are methods and kits for isothermal nucleic acid amplifications that use an oligocation-oligonucleotide conjugate primer for amplifying a target nucleic acid to generate amplicons. Isothermal DNA amplification methods that employ a strand displacing DNA polymerase and polyamine-oligonucleotide conjugate primer are also provided.

9 Claims, 3 Drawing Sheets

ISOTHERMAL AMPLIFICATION USING OLIGOCATION-CONJUGATED PRIMER SEQUENCES

FIELD OF INVENTION

The invention generally relates to methods and kits for performing isothermal amplification reactions employing oligocation-oligonucleotide conjugate primers. The oligocation-oligonucleotide conjugate primer comprises an oligocation moiety covalently conjugated at 5' end of an oligonucleotide sequence.

BACKGROUND

DNA amplification is a process of replicating a target double-stranded DNA (dsDNA) to generate multiple copies. Since individual strands of a dsDNA are antiparallel and complementary, each strand may serve as a template strand for the production of its complementary strand. The template strand is preserved as a whole or as a truncated portion and the complementary strand is assembled from deoxynucleoside triphosphates (dNTPs) by a DNA polymerase. The complementary strand synthesis proceeds in 5'→3' direction starting from the 3' terminal end of a primer sequence that is hybridized to the template strand. A variety of efficient nucleic acid amplification techniques are currently available such as polymerase chain reaction (PCR), ligase chain reaction (LCR), self-sustained sequence replication (3SR), nucleic acid sequence based amplification (NASBA), strand displacement amplification (SDA), multiple displacement amplification (MDA), or rolling circle amplification (RCA). Many of these techniques generate a large number of amplified products in a short span of time.

Whole-genome amplification (WGA) involves non-specific amplification of a target DNA. WGA is often achieved by MDA employing random oligonucleotide primers (e.g., NNNNN*N) for priming the DNA synthesis at multiple locations of the target DNA along with a high fidelity DNA polymerase having a strand displacing activity (e.g., Phi29 polymerase). Even though currently available commercial WGA systems such as GenomiPhi (GE Healthcare, USA) and RepliG (Qiagen) kits provide optimal results with an input DNA of 1 nanogram or more, performance of these systems is poor when the target DNA is available only in smaller quantities or when amplification of DNA from a few or single cells is performed.

Amplification of trace amounts of target DNA using conventional methods often results in incomplete amplification of DNA sequences leaving "dropouts" in sequence coverage and amplification bias wherein DNA sequences are amplified unevenly. Further, products of the amplification reaction (amplicons) may often anneal among themselves leading to the generation of undesirable chimeric products. Efficient methods for non-specifically amplifying trace amounts of target DNA are therefore highly desirable.

BRIEF DESCRIPTION

In some embodiments, nucleic acid amplifications are provided that use an oligocation-oligonucleotide conjugate primer for amplifying a target nucleic acid to generate amplicons.

In some embodiments, an isothermal amplification method for producing at least one amplicon based on a target DNA is provided. The method comprises the steps of, providing the target DNA, providing a DNA amplification reaction mixture comprising an oligocation-oligonucleotide conjugate primer, a DNA polymerase having a strand displacement activity, and a dNTP mixture, and amplifying at least one portion of the target DNA using the DNA amplification reaction mixture to produce at least one amplicon. The oligocation-oligonucleotide conjugate primer used in the amplification reaction comprises an oligocation moiety covalently conjugated to the 5' end of an oligonucleotide sequence.

In some embodiments, a method of producing at least one amplicon based on a target DNA is provided, wherein the method comprises the steps of, providing the target DNA, annealing at least one oligocation-oligonucleotide conjugate primer to the target DNA to generate a target DNA:primer hybrid, and extending the oligocation-oligonucleotide conjugate primer in the target DNA:primer hybrid via an isothermal nucleic acid amplification reaction to produce at least one amplicon complementary to at least one portion of the target DNA. The oligocation-oligonucleotide conjugate primer that is used in the method comprises an oligocation moiety covalently conjugated to the 5' end of an oligonucleotide sequence.

In some embodiments, kits for isothermal DNA amplification are provided. The kits comprise a DNA polymerase having strand displacement activity and an oligocation-oligonucleotide conjugate primer, wherein the oligocation-oligonucleotide conjugate primer comprises an oligocation moiety covalently conjugated to the 5' end of an oligonucleotide sequence.

DRAWINGS

These and other features, aspects and advantages of the invention will become better understood when the following detailed description is read with reference to the accompanying figures.

DETAILED DESCRIPTION

To more clearly and concisely describe and point out the subject matter of the claimed invention, the following definitions are provided for specific terms, which are used in the following description and the appended claims.

As used herein, the term "target DNA" refers to a DNA sequence of either natural or synthetic origin that is desired to be amplified in a DNA amplification reaction. The target DNA acts as a template in a DNA amplification reaction. Either a portion of a target DNA or the entire region of a target DNA may get amplified by a DNA polymerase in a DNA amplification reaction to produce amplification products or amplicons. Amplicons may include multiple copies of the target DNA or multiple copies of sequences that are complementary to the target DNA. The target DNA may be obtained from a biological sample in vivo or in vitro. For example, the target DNA may be obtained from a bodily fluid (e.g., blood, blood plasma, serum, or urine), an organ, a tissue, a cell, a sectional portion of an organ or tissue, a cell isolated from a biological subject (e.g., a region containing diseased cells, or circulating tumor cells), a forensic sample or an ancient sample. The biological sample that contains, or is suspected to contain, the target DNA may be of eukaryotic origin, prokaryotic origin, viral origin or bacteriophage origin. For example, the target DNA may be obtained from an insect, a protozoa, a bird, a fish, a reptile, a mammal (e.g., rat, mouse, cow, dog, guinea pig, or rabbit), or a primate (e.g., chimpanzee or human). The target DNA may also be a complementary DNA (cDNA) that is generated from an RNA template (e.g., mRNA, ribosomal RNA) using a reverse transcriptase enzyme. A DNA product generated by another reaction, such as a ligation reaction, a PCR reaction, or a synthetic DNA may also serve as a suitable target DNA. The target DNA may be dispersed in solution or may be immobilized on a solid support, such as in blots, arrays, glass slides, microtiter plates, beads or ELISA plates.

As used herein the term "oligonucleotide" refers to an oligomer of nucleotides. A nucleotide may be represented by its letter designation using alphabetical letters corresponding to its nucleoside. For example, A denotes adenosine, C denotes cytidine, G denotes guanosine, U denotes uridine, and T denotes thymidine (5-methyl uridine). W denotes either A or T/U, and S denotes either G or C. N represents a random nucleoside and may be any of A, C, G, or T/U. A star (*) sign preceding a letter designation denotes that the nucleotide designated by the letter is a phosphorothioate-modified nucleotide. For example, *N represents a phosphorothioate-modified random nucleotide. A plus (+) sign preceding a letter designation denotes that the nucleotide designated by the letter is a locked nucleic acid (LNA) nucleotide. For example, +A represents an adenosine LNA nucleotide, and +N represents a locked random nucleotide. The oligonucleotide may be a DNA oligonucleotide, an RNA oligonucleotide or a DNA-RNA chimeric sequence. Whenever an oligonucleotide is represented by a sequence of letters, the nucleotides are in 5'→3' order from left to right. For example, an oligonucleotide represented by a letter sequence $(W)_x (N)_y (S)_z$, wherein x=2, y=3 and z=1, represents an oligonucleotide sequence WWNNNS, wherein W is the 5' terminal nucleotide and S is the 3' terminal nucleotide ("Terminal nucleotide" refers to a nucleotide that is located at a terminal position of an oligonucleotide sequence. The terminal nucleotide that is located at a 3' terminal position is referred as a 3' terminal nucleotide, and the terminal nucleotide that is located at a 5' terminal position is referred as a 5' terminal nucleotide).

As used herein the term "nucleotide analogue" refers to compounds that are structurally analogous to naturally occurring nucleotides. The nucleotide analogue may have an altered phosphate backbone, sugar moiety, nucleobase, or combinations thereof. Nucleotide analogues may be a synthetic nucleotide, a modified nucleotide, or a surrogate replacement moiety (e.g., inosine). Generally, nucleotide analogues with altered nucleobases confer, among other things, different base pairing and base stacking proprieties.

As used herein, the term "primer" or "primer sequence" refers to a linear oligonucleotide that hybridizes to a target DNA template to generate a target DNA:primer hybrid and to prime a DNA synthesis reaction. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the predetermined nucleic acid sequence in the target nucleic acid. Generally, suitable primer lengths are in the range of about 3 nucleotides long to about 40 nucleotides long. The primer may be an RNA oligonucleotide, a DNA oligonucleotide, or a chimeric sequence.

As used herein, the term "random oligonucleotide" refers to a mixture of oligonucleotide sequences, generated by randomizing a nucleotide at any given location in an oligonucleotide sequence in such a way that the given location may consist of any of the possible nucleotides or their analogues (complete randomization). A random oligonucleotide when used as a random primer represents a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown or for whole-genome amplification reaction.

As described herein, "partially constrained oligonucleotide" refers to a mixture of oligonucleotide sequences, generated by completely randomizing some of the nucleotides of an oligonucleotide sequence (e.g., the nucleotide may be any of A, T/U, C, G, or their analogues) while restricting the complete randomization of some other nucleotides (e.g., the randomization of nucleotides at certain locations are to a lesser extent than the possible combinations A, T/U, C, G, or their analogues). A partially constrained oligonucleotide may be used as primer sequence. For example, a partially constrained DNA hexamer primer represented by WNNNNN, represents a mixture of primer sequences wherein the 5' terminal nucleotide of all the sequences in the mixture is either A or T. Here, the 5' terminal nucleotide is constrained to two possible combinations (A or T) in contrast to the maximum four possible combinations (A, T, G or C) of a completely random DNA primer (NNNNNN). Suitable primer lengths of a partially constrained primer may be in the range of about 3 nucleotides long to about 15 nucleotides long.

As used herein the term "oligocation-oligonucleotide conjugate primer" refers to a primer sequence wherein a linear oligonucleotide is covalently conjugated to an oligocation. Oligocation comprises one or more cationic moiety. Often oligocation is an oligomer of a cationic moiety. Oligocation-conjugated random primers are positive-charge modified primers with random sequence.

As used herein the dNTP mixture refers to a mixture deoxyribonucleoside triphosphates, where N is a random nucleotide including any of A, C, G, or T/U.

As used herein, the terms "strand displacing nucleic acid polymerase" or "a polymerase having strand displacement activity" refer to a nucleic acid polymerase that has a strand displacement activity apart from its nucleic acid synthesis activity. A strand displacing nucleic acid polymerase can continue nucleic acid synthesis on the basis of the sequence of a nucleic acid template strand by reading the template strand while displacing a complementary strand that is annealed to the template strand.

As used herein, multiple displacement amplification (MDA) refers to a nucleic acid amplification method, wherein the amplification involves the steps of annealing a primer to a denatured nucleic acid followed by DNA synthesis in which downstream double stranded DNA region(s) which would block continued synthesis is disrupted by a strand displacement nucleic acid synthesis through these regions. As nucleic acid is synthesized by strand displacement, single stranded DNA is generated by the strand displacement, and as a result, a gradually increasing number of priming events occur, forming a network of hyper-branched nucleic acid structures. MDA is highly useful for whole-genome amplification for generating high-molecular weight DNA from a small amount of genomic DNA sample with limited sequence bias. Any strand displacing nucleic acid polymerase that has a strand displacement activity apart from its nucleic acid synthesis activity (e.g., Phi29 DNA polymerase or a large fragment of the Bst DNA polymerase) may be used in MDA. MDA is often performed under isothermal reaction conditions, using random primers for achieving amplification with limited sequence bias.

As used herein, the term "rolling circle amplification (RCA)" refers to a nucleic acid amplification reaction that amplifies a circular nucleic acid template (e.g., single stranded DNA circles) via a rolling circle mechanism. RCA is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). RCA typically produces concatamers comprising tandem repeat units of the circular nucleic acid template sequence complement.

In some embodiments, methods that employ an oligocation-oligonucleotide conjugate primer for amplifying a target nucleic acid to generate amplicons are provided. An oligocation-oligonucleotide primer comprises an oligocation moiety that is covalently attached to the 5' terminal end of an oligonucleotide primer sequence. For example, a chemical moiety comprising one or more cationic spermine units (e.g., a monomeric or dimeric unit of spermine) may be covalently coupled to the 5' terminal end of an oligonucleotide primer sequence (e.g., a random hexamer sequence). Covalent attachment of a positively charged, cationic spermine derivative to the 5' end of the random primer sequence may alleviate some of the electrostatic repulsion from the negatively charged phosphodiester bonds upon hybridization of the oligonucleotide primer sequence to a target nucleic acid (e.g., a target DNA).

Use of oligocation-oligonucleotide conjugate primer in nucleic acid amplification reactions enhances the target recognition of the primers and also increases the hybridization efficiency of the primer to the target nucleic acid. Further, melting temperature of target nucleic acid-primer hybrid is increased when an oligocation-oligonucleotide primer is employed in the nucleic acid amplification reaction. Hence, high stringent hybridization conditions may be employed in nucleic acid amplification reactions to reduce undesired amplification products and artifacts. High stringent hybridization conditions refer to reaction conditions that impart a higher stringency to an oligonucleotide hybridization event than the stringency provided by conditions that are generally used for nucleic acid amplification reactions. For example, a high stringent hybridization condition may be achieved in a nucleic acid amplification reaction by increasing the reaction temperature or by decreasing the salt concentration. Nucleic acid amplification reactions are often carried out at about 75 mM salt concentration. In contrast, if a nucleic acid amplification reaction is performed at about 15 mM salt concentration, it may offer a high stringent hybridization condition. High stringent hybridization condition may be provided in an in-vitro isothermal nucleic acid amplification reaction by increasing the temperature from about 30° C., which is often used. For example, the isothermal nucleic acid amplification reaction that uses an oligocation-oligonucleotide conjugate primer may be performed at about 35° C. to about 45° C. to provide a high stringent hybridization condition.

In some embodiments, an isothermal amplification method for producing at least one amplicon based on a target DNA is provided. The method comprises the steps of, providing the target DNA; providing a DNA amplification reaction mixture comprising an oligocation-oligonucleotide conjugate primer, a DNA polymerase having a strand displacement activity, and a dNTP mixture; and amplifying at least one portion of the target DNA using the DNA amplification reaction mixture to produce the at least one amplicon. The oligocation-oligonucleotide conjugate primer used in the amplification reaction comprises an oligocation moiety that is covalently conjugated to the 5' end of an oligonucleotide sequence. The oligocation moiety may be covalently conjugated to the 5' end of an oligonucleotide sequence by using any of the synthetic methods (e.g., phosphoramidite synthesis) used for conjugation. Even though the oligocation-oligonucleotide conjugate primer hybridizes to the target nucleic acid with higher efficiency, such primers do not inhibit the strand displacement amplification. Further, the oligocation covalently conjugated to the 5' end of an oligonucleotide (primer) sequence does not interfere with the DNA polymerase binding and primer extension reaction.

By attachment of an oligocation moiety the overall negative charge of an oligonucleotide sequence is reduced. This charge reduction decreases the electrostatic charge repulsion and increases the melting temperature of the oligonucleotide sequence that further improves hybridization properties. Attachment of the oligocation moiety at the 5' end of the oligonucleotide sequence preserves the oligonucleotide structure and its ability to act as a substrate for DNA processing enzymes such as a DNA polymerase.

The oligonucleotide sequence in the oligocation-oligonucleotide conjugate primer may be a specific primer sequence, a random primer sequence or a partially constrained random primer sequence. Specific primer sequences are complementary, in the Watson-Crick sense, to a particular sequence that is present in the target DNA template. Specific oligonucleotide sequences may be employed in oligocation-oligonucleotide conjugate primer, for example, for specifically amplifying a mitochondiral DNA in a mixture, a certain plasmid in a mixture, or certain genome region. In some embodiments, the oligonucleotide sequence in the oligocation-oligonucleotide conjugate primer is a random primer sequence. For example, the oligonucleotide sequence in the oligocation-oligonucleotide conjugate primer may be NN $(N)_m$NN, where the integer value of m ranges from 0 to 36. In some embodiments, the integer value of m may range from 0 to 20. In some other embodiments, the integer value of m may range from 0 to 10. In some example embodiments, the oligonucleotide sequence may be a random a random tetramer, a random pentamer, a random hexamer, a random heptamer or a random octamer. The oligocation-oligonucleotide conjugate primer may comprise natural, synthetic or modified nucleotides, or nucleotide analogues.

In some embodiments, the oligocation-oligonucleotide conjugate primer may comprise synthetic backbones or nucleotide analogues that confer stability and/or other advantages (e.g., secondary structure formation) to the primers (e.g., peptide nucleic acid (PNA), locked nucleic acid) or may comprise modified sugar moieties (e.g., xylose nucleic acid or analogues thereof). In some embodiments, the oligonucleotide sequence in the oligocation-oligonucleotide conjugate primer comprises one or more LNA nucleotides. LNA nucleotide contains a bicyclic furanose sugar unit locked in a ribonucleic acid-mimicking sugar conformation. The structural change from a deoxyribonucleotide (or a ribonucleotide) to the LNA nucleotide may be limited from a chemical perspective, for example, the introduction of an additional linkage between carbon atoms at 2' position and 4' position (e.g., 2'-C, 4'-C-oxymethylene linkage). The 2' and 4' position of the furanose unit in the LNA nucleotide may be linked by an O-methylene (e.g., oxy-LNA: 2'-O, 4'-C-methylene-β-D-ribofuranosyl nucleotide), a S-methylene (thio-LNA), or a NH-methylene moiety (amino-LNA), and the like. Such linkages restrict the conformational freedom of the furanose ring. Oligocation-oligonucleotide conjugate primers comprising one or more LNA oligonucleotides display enhanced hybridization affinity toward complementary single-stranded RNA, single-stranded DNA or double-stranded DNA. Further, inclusion of LNA in the oligonucleotide may induce A-type (RNA-like) duplex conformations.

In some embodiments, the oligocation-oligonucleotide conjugate primer employed for DNA amplification reaction may be resistant to nucleases, for example an exonuclease. For example, the oligonucleotide sequence in the oligocation-oligonucleotide conjugate primer may comprise one or more modified phosphate linkage (e.g., a phosphorothioate linkage) to render it exonuclease-resistant. In some embodiments, the oligocation-oligonucleotide conjugate primer comprises an exonuclease-resistant random oligonucleotide sequence. For example, the oligonucleotide of the conjugate primer may have a random sequence such as NNNNN*N or NNNN*N*N.

In some embodiments, the oligocation moiety in the oligocation-oligonucleotide conjugate primer include, but is not limited to, cationic polyamines (e.g., spermidine, spermine or putrescine, chemical moieties comprising one or more of NH units or NC(NH2)2 units), or peptides containing cationic side chains (e.g., peptides comprising lysine residues). For example, an oligocation moiety comprising one or more spermine moieties may be covalently conjugated to the 5' terminal end of an oligonucleotide primer sequence to generate an oligocation-oligonucleotide conjugate primer. In some other embodiments, the cationic polyamine may be a chemical moiety that is derived from a cationic spermine moiety. In some embodiments, the oligocation moiety may comprise a cationic polyamine along with one or more anionic groups. However, the net charge of the oligocation moiety shall be at least +1 under the conditions employed for DNA amplification reactions. For example, the nitrogen atoms in spermine have pKas ranging from about 8.5 to 11.5 depending on the position. Hence the DNA amplification reaction using spermine-containing primers may be performed in buffers having pH values such that one or more nitrogen are protonated at the reaction condition. For example, a buffer having a pH of less than about 8.0 at room temperature and a pH of 7.8 at 30° C. may be used for the DNA amplification reaction. The number of cationic groups that may be attached to the 5' end of a oligonucleotide primer sequence without adversely affecting the solubility coefficient of the resultant oligocation-oligonucleotide conjugate primer may be dependent on various factors, including but not limited to, net charge of each cationic group, length of the oligonucleotide primer sequence and/or the length of the oligocation moiety.

In some example embodiments, the oligocation-oligonucleotide conjugate primer has a general chemical structure as depicted in structure I. The integer value of n in structure I represents the number of spermine units in the oligocation-oligonucleotide conjugate primer. The integer value of n may range from 1 to 5. The length of the oligonucleotide sequence in structure I may range from a 6-mer to a 20-mer sequence. In some embodiments, a single spermine unit (n=1) may be covalently conjugated to the 5' terminal nucleotide of a hexamer (6-mer) sequence without compromising the solubility of the resultant oligocation-oligonucleotide conjugate primer. In some other embodiments, an oligocation comprising two or three spermine moieties may be covalently coupled to the 5' terminal nucleotide of oligonucleotides ranging from 8 to 15-mers. Covalent coupling of oligocations comprising 4 or 5 spermine moieties may be performed on a 16-mer oligonucleotide or a 20-mer oligonucleotide respectively without adversely affecting the solubility coefficient of the resultant oligocation-oligonucleotide conjugate primer. The covalent conjugation of the oligocation moiety to an oligonucleotide primer sequence alters the overall charge of the oligonucleotide primer sequence. Each spermine unit in structure I increases the overall charge of the oligonucleotide sequence by +3, with an overall charge calculated by the formula 3n−(m−1) where n equals the number of spermine units and m equals the number of bases in the oligonucleotide. For example, in structure I, when n=3 the overall charge of the oligonucleotide sequence is altered by +9 (+3n).

Structure I

In some embodiments, oligocation-oligonucleotide conjugate primer employed in the DNA amplification reaction comprises a random oligonucleotide sequence covalently attached to a spermine unit-containing cationic polyamine. In some embodiments, the oligocation-oligonucleotide conjugate primer has a formula as depicted in structure II. In structure II, the integer value of n may range from 1 to 5 and integer value of m may range from 0 to 36.

Structure II

In some embodiments, the oligocation-oligonucleotide conjugate primer employed in the DNA amplification reaction is a nuclease-resistant primer. In some embodiments, the nuclease-resistant oligocation-oligonucleotide conjugate primer has a general structure of structure III. The integer value of n may range from 1 to 5 and integer value of m may range from 0 to 36.

Structure III

In some embodiments, oligocation-oligonucleotide conjugate primer employed in the DNA amplification reaction is a nuclease-resistant hexamer primer, having structure IV. The integer value of n may be 1 or 2 in structure IV.

Structure IV

In some embodiments, the oligocation-oligonucleotide conjugate primer employed in the DNA amplification reaction is a nuclease-resistant random hexamer primer, represented by structure V. The random primer comprises a polyamine comprising two spermine units, wherein the polyamine is covalently conjugated to the 5' terminal nucleotide of a random hexamer. The random hexamer primer further comprises a phosphorothioate linkage between its 3' terminal nucleotide and the nucleotide adjacent to the 3' terminal nucleotide.

cation-oligonucleotide conjugate primer. In some embodiments, a polyamine comprising of a poly-lysine moiety consisting of 5 lysine monomer units (a pentamer) having a molecular weight of 640 Da is covalently attached to the 5' end of an oligonucleotide sequence. The lysine containing oligonucleotide conjugate primer may be synthesized by any of the art-recognized protocols (e.g., Nucleic Acid Research 1998, 26, 3136-3145).

In some embodiments, methods for producing at least one amplicon based on a target DNA comprise the steps of, providing the target DNA, annealing at least one oligocation-oligonucleotide conjugate primer to the target DNA to generate a target DNA:primer hybrid, and extending the oligocation-oligonucleotide conjugate primer via an isothermal nucleic acid amplification reaction to produce at least one amplicon that is complementary to at least one portion of the target DNA. The oligocation-oligonucleotide conjugate Structure V In some embodiments, a polyamine, comprising at least one lysine moiety, may be covalently conjugated to the 5' end of an oligonucleotide primer sequence to generate the oligoprimer that is used in the method comprises an oligocation moiety that is covalently conjugated to the 5' end of an oligonucleotide sequence.

The target DNA may be linear template, nicked template or a circular template. It may be a natural or synthetic DNA. The target DNA may be a cDNA or a genomic DNA. The DNA template may be a synthetic template (e.g., a linear or nicked DNA circularized by enzymatic/chemical reactions), or it may be a plasmid DNA.

An oligocation-oligonucleotide conjugate primer depicted in structure I may be employed in the method. The oligonucleotide moiety in the conjugate primer may be a specific sequence, a random sequence or a partially constrained random sequence. For example, the oligonucleotide may be random pentamer sequence or a random hexamer sequence. Further, the random sequence may comprise one or more modified nucleotides and may comprise one or more phosphorothioate linkages.

In some embodiments, the oligonucleotide sequence of structure I is a partially constrained primer sequence. Non-limiting examples of partially constrained primer sequences, that have restricted randomization only at the terminal nucleotides include, but is not limited to, $W(N)_yS$, $S(N)_yW$, $D(N)_yG$, $G(N)_yD$, $C(N)_yA$, or $A(N)_yC$. The integer value of y may be in the range 2 to 13. In some embodiments, the value of y may be 2, 3, 4, or 5. In some example embodiments, a partially constrained primer sequence, $(W)_x(N)_y(S)_z$, wherein x, y and z are integer values independent of each other, and wherein value of x is 2 or 3, value of y is 2, 3, 4, or 5 and value of z is 1 or 2 may be employed as the oligonucleotide sequence in structure I. The partially constrained primer sequence of may comprise one or more nucleotide analogues. In some embodiments, the partially constrained primer sequence may have a terminally mismatched primer-dimer structure. For example, since W cannot base pair with S, there will be a terminal mismatch at both the 3' terminal nucleotides if the primer-dimer structure without any recessed ends is formed by inter-molecular hybridization. In some embodiments, the oligonucleotide sequence of structure I is a nuclease-resistant, partially constrained primer sequence comprising a modified nucleotide, and having terminal mismatch primer-dimer structure. Suitable oligonucleotide sequences that may be part of structure I include, but are not limited to, +W+WNNS, W+W+NNS, +W+WNNNS, W+W+NNNS, W+W+NN*S, +W+WNN*S, W+W+NNN*S, +W+WNNN*S, W+W+N*N*S, +W+WN*N*S, W+W+NN*N*S, or +W+WNN*N*S.

In some embodiments, the oligonucleotide-oligocation primer depicted in any of structures II to V may be employed for the isothermal DNA amplification reaction using a strand displacing DNA polymerase. In some example embodiments, the DNA amplification methods employ an oligocation-oligonucleotide conjugate primer that has a structure of structure V, which is the general structure of structure IV, wherein integer value of n is 2.

The nucleic acid polymerase used for the isothermal amplification methods may be a proofreading or a non-proofreading nucleic acid polymerase. The nucleic acid polymerase may be a thermophilic or a mesophilic nucleic acid polymerase. Examples of DNA polymerases that are suitable for use in the methods include, but are not limited to, Phi29 DNA polymerase, hi-fidelity fusion DNA polymerase (e.g., *Pyrococcus*-like enzyme with a processivity-enhancing domain, New England Biolabs, MA), Pfu DNA polymerase from *Pyrococcus furiosus* (Strategene, Lajolla, Calif.), Bst DNA polymerase from *Bacillus stearothermophilus* (New England Biolabs, MA), Sequenase™ variant of T7 DNA polymerase, exo(−) Vent$_R$™ DNA polymerase (New England Biolabs, MA), Klenow fragment from DNA polymerase I of *E. coli*, T7 DNA polymerase, T4 DNA polymerase, DNA polymerase from *Pyrococcus* species GB-D (New England Biolabs, MA), or DNA polymerase from *Thermococcus litoralis* (New England Biolabs, MA).

In some embodiments, the nucleic acid polymerase used for the isothermal amplification is a strand displacing nucleic acid polymerase. The methods may employ a highly processive, strand-displacing polymerase to amplify the target DNA under conditions for high fidelity base incorporation. A high fidelity DNA polymerase refers to a DNA polymerase that, under suitable conditions, has an error incorporation rate equal to or lower than those associated with commonly used thermostable PCR polymerases such as Vent DNA polymerase or T7 DNA polymerase (from about $1.5 \times 10^{-5}$ to about $5.7 \times 10^{-5}$). In some embodiments, a Phi29 DNA polymerase or Phi29-like polymerase may be used for amplifying a DNA template. In some embodiments, a combination of a Phi29 DNA polymerase and a Taq DNA polymerase may be used for the circular DNA amplification.

Additional enzymes may be included in the isothermal amplification reaction mixture to minimize mis-incorporation events. For example, protein-mediated error correction enzymes, such as, MutS, may be added to improve the DNA polymerase fidelity either during or following the DNA polymerase reaction.

In some embodiments, at least one amplicon is produced from a circular target DNA template by rolling circle amplification. The amplification reagents including a DNA polymerase, oligocation-oligonucleotide conjugate primer, and dNTPs may be added to the target DNA to produce an amplification reaction mixture for initiating an RCA reaction. The amplification reaction mixture may further include reagents such as single-stranded DNA binding proteins and/or suitable amplification reaction buffers. After or during the amplification reaction, amplicons may be detected by any of the currently known methods for DNA detection. RCA may be a linear RCA (LRCA), exhibiting linear amplification kinetics (e.g., RCA using a single specific primer), or may be an exponential RCA (ERCA) exhibiting exponential amplification kinetics. RCA may also be performed using multiple oligocation-oligonucleotide conjugate primers (multiply primed rolling circle amplification or MPRCA) leading to hyper-branched concatemers. For example, in a double- Structure V primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. In some example embodiments, an RCA is performed in vitro under isothermal conditions using a suitable nucleic acid polymerase such as Phi29 DNA polymerase.

In some other embodiments, a linear DNA template may be amplified using MDA. Conventional methods of MDA often result in decreased amplification speed and highly sequence-biased amplification. In contrast, usage of oligocation-oligonucleotide conjugate primer in MDA reaction promoted faster DNA amplification kinetics and improved DNA sequence coverage and balance. Further, the increase in Tm of the target DNA:primer hybrid when oligocation-oligonucleotide conjugate primer are used allows the MDA reaction to be performed under more stringent conditions, such as at a higher temperature or with a lower concentration of salt (e.g., 15 mM KCl as opposed to 75 mM under otherwise standard conditions) or allows use of more stringent buffers for high stringent hybridization conditions. Such stringent reaction further decreases unwanted reaction intermediates and products such as formation of chimeric products by self-hybridization.

Further, usage of oligocation-oligonucleotide conjugate primer in amplification reactions allows for robust amplification of trace DNA samples under a wider variety of conditions, including but not limited to, circulating plasma DNA, DNA isolated from formalin fixed paraffin-embedded (FFPE) samples, forensics DNA samples that have been exposed to environmental conditions or ancient DNA samples. The amplified library comprising the amplicons may further be used for targeted detection of amplified sequences via qPCR or sequencing.

In some embodiments, a kit for isothermal DNA amplification is provided. The kit comprises a DNA polymerase having strand displacement activity and an oligocation-oligonucleotide conjugate primer, wherein the oligocation-oligonucleotide conjugate primer comprises an oligocation moiety covalently conjugated to the 5' end of an oligonucleotide sequence.

In some embodiments, the kit comprises a Phi29 DNA polymerase. The kit may comprise the oligocation-oligonucleotide conjugate primer having a chemical structure as depicted in structures I to V. The integer value of n in structures I to III may range from 1 to 5 and the oligonucleotide sequence may range from a 6-mer to a 20-mer sequence. In some embodiments, the kit comprises an oligocation-oligonucleotide conjugate primer wherein a single spermine unit (n=1) is covalently conjugated to the 5' terminal nucleotide of a hexamer (6-mer) sequence. In some other embodiments, the kit comprises an oligocation-oligonucleotide conjugate primer wherein an oligocation comprising two or three spermine moieties is covalently coupled to the 5' terminal nucleotide of oligonucleotides ranging from 8 to 15-mers. In some other embodiments the kit comprises an oligocation-oligonucleotide conjugate primer wherein oligocations comprising 4 or 5 spermine moieties is coupled with a 16-mer oligonucleotide or a 20-mer oligonucleotide respectively. In some embodiments, the kit comprises an oligocation-oligonucleotide conjugate primer having a general structure of structure IV, wherein the integer value of n may be 1 or 2. In some example embodiments, the kit comprises an oligocation-oligonucleotide conjugate primer having a structure V.

The methods and kits described herein may be used for amplifying and analyzing DNA samples such as those for forensic analysis, bio-threat identification, or medical analysis. The sensitivity of the method allows for the whole-genome amplification of single bacterial and eukaryotic cells for whole genome amplification for downstream testing and analysis. Further, use of oligocation-oligonucleotide conjugate primers promotes faster DNA amplification kinetics, higher sensitivity for low input DNA quantities, and less biased, more balanced amplification. Further, these modified primers that bind more strongly allows amplification reaction conditions to be modified to decrease the stability of DNA synthesis self-hybridization events.

The following examples are disclosed herein for illustration only and should not be construed as limiting the scope of the invention. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min.": minutes and "h.": hours.

EXAMPLES

Example 1

Reaction Kinetics and Sensitivity of MDA Reactions Utilizing Spermine-Modified Random Hexamer Primer Amplification reactions were performed using 10 µM of a random primer or an oligocation-oligonucleotide conjugate primer to determine the effect of an oligocation-oligonucleotide conjugate primer on MDA reactions. An exonuclease resistant, standard random hexamer primer having a sequence, NNNN*N*N, was used as the random primer. A 2-SP-modified hexamer primer sequence, 5' SP2-NNNNN*N (metabion international AG, Germany) wherein an oligocation moiety comprising a dimeric spermine moiety was covalently conjugated to the 5' terminal end of an exonuclease resistant, random hexamer sequence, NNNNN*N ("SP2" represents structure IV with n=2; two units of the spermine modification attached to the 5' end of the DNA sequence) was used as the oligocation-oligonucleotide conjugate primer. Real-time amplification of Bacillus subtilis chromosomal DNA (target DNA template) was performed using a dilution series ranging from 1 ng to 1 fg. DNA was denatured by adding an equal volume of lysis buffer (0.4M KOH, 100 mM DTT, 0.02% Tween-20), incubated for 5 minutes, and neutralized with one volume of neutralization buffer (0.4M HCl, 0.6M Tris, pH 7.5). Reactions (12 µL) contained 50 mM HEPES, pH 8.0, 20 mM $MgCl_2$, 0.01% Tween-20, 1 mM TCEP, 2.5% PEG-8000, 5 mM KCl, 10 µM random hexamer or 10 µM SP2-NNNNN*N, 20 µg/ml Phi29 polymerase, SYBR Green I dye (Invitrogen) at 1:20,000 dilution, and 1 µL containing the indicated concentrations of B. subtilis genomic DNA. Incubation was at 30° C. for 5 hours. The amplification reaction was monitored real time by monitoring the fluorescence increase over time in a Tecan plate reader (Tecan SNiPer, Amersham-Pharmacia Biotech).

Figure 1:
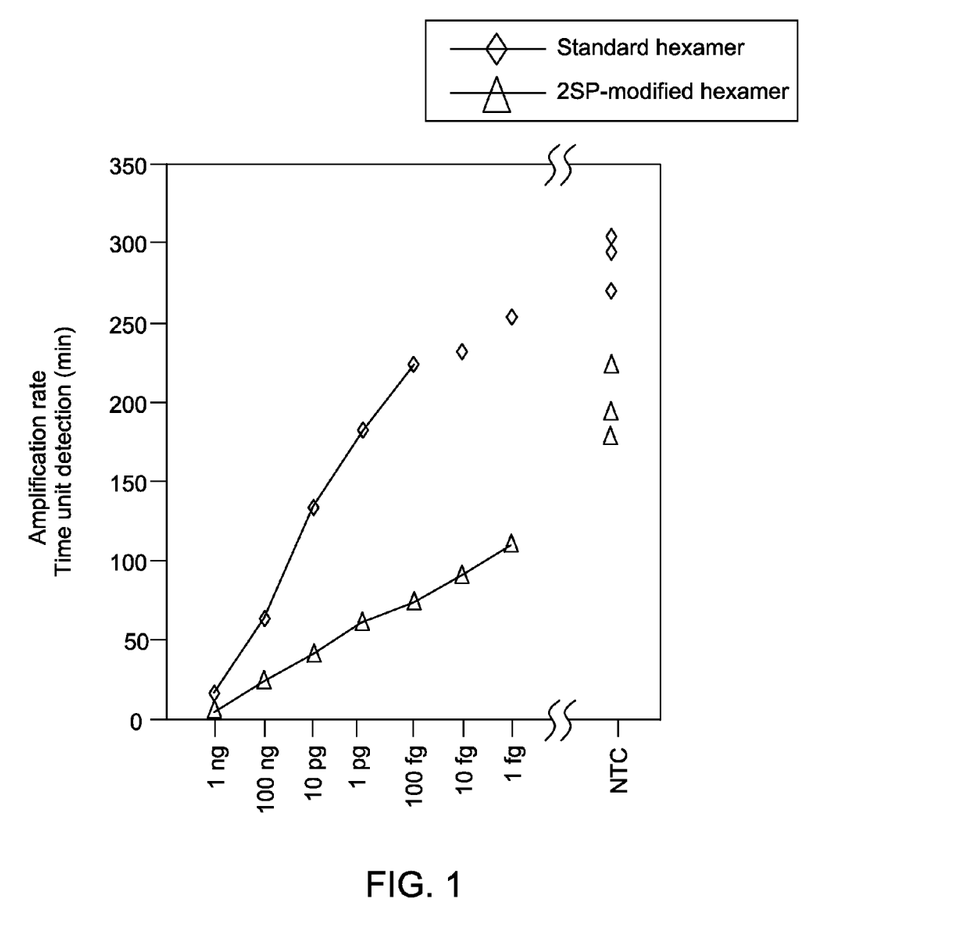
FIG. 1 illustrates the effectiveness of a spermine-modified random hexamer primer to increase the kinetics and sensitivity of an MDA reaction.

FIG. 1 illustrates the amplification rate of standard random hexamer primer (NNNN*N*N) and the spermine-modified random hexamer primer (SP2-NNNNN*N). The amplification rate for each of the dilution series was estimated by monitoring the time taken for the generation of detectable levels of amplicon products in each of the dilution series. NTC represents the "no template control" wherein the amplification reaction was performed without the addition of a target DNA template. FIG. 1 shows an increased reaction kinetics and sensitivity of MDA reaction when spermine-modified random primers were used for amplification reaction. Substituting the standard random hexamer with the 5'-SP2-NNNNN*N hexamer (2SP-modified hexamer) provided increased amplification speed (approximately 3-fold) and allowed femtogram quantities of DNA to be amplified efficiently. Unexpectedly, the presence of the charged species at the 5' end of the short primer did not inhibit binding and extension by DNA polymerase. Further, the charged species did not inhibit strand displacement of the primer by the DNA polymerase during isothermal strand displacement amplification. Strand displacement of the modified primer is required, as upstream amplicon generation proceeds through downstream primed and extended sections in MDA reactions. If the primer modification inhibited initiation of extension by the DNA polymerase, or strand displacement by the DNA polymerase, kinetics would have been slow, and yield would have been low.

Example 2

Figure 2:
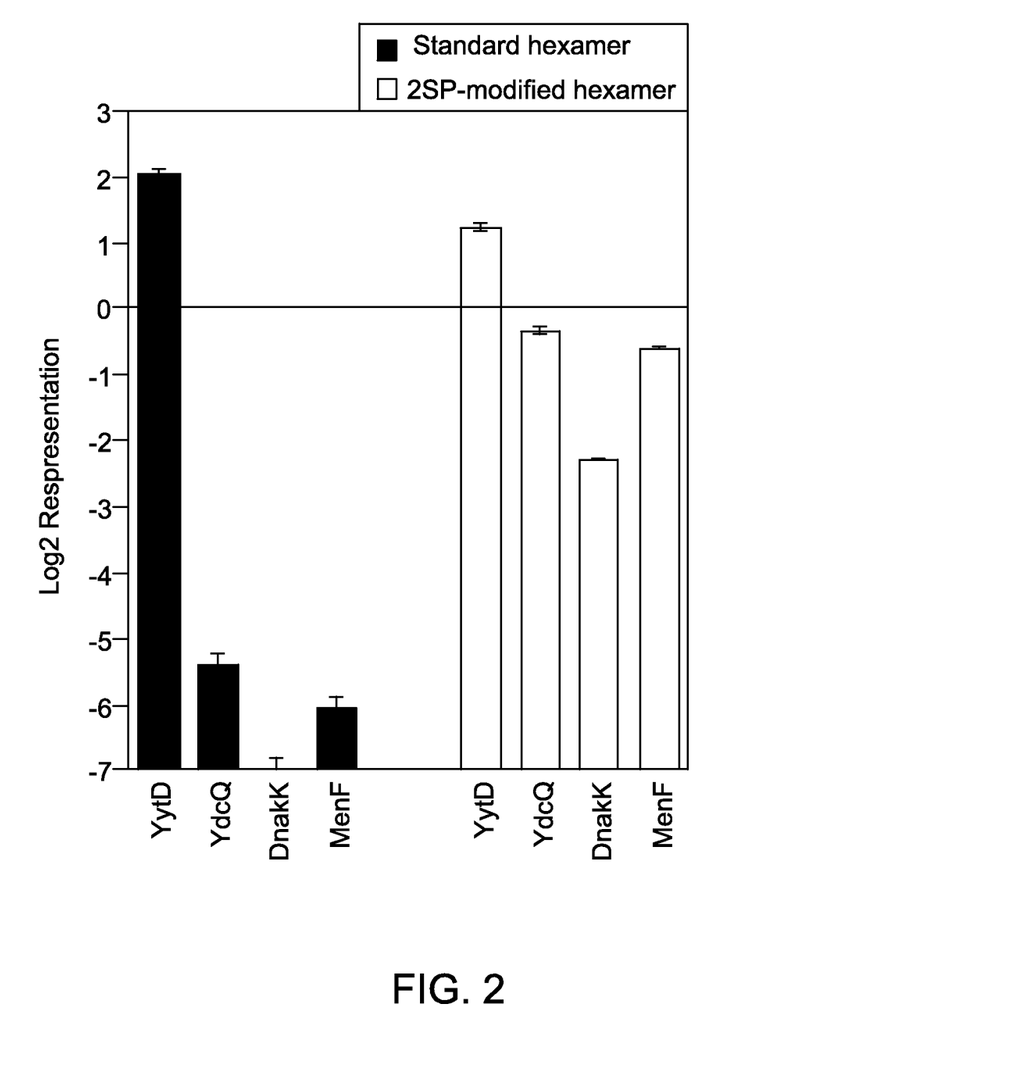
FIG. 2 illustrates the effectiveness of a spermine-modified random hexamer primer to increase the sequence coverage and amplification balance of a DNA amplification reaction.

Sequence Coverage and Amplification Balance of Amplification Reactions Utilizing Spermine-Modified Random Hexamer Primer 100 fg of *Bacillus subtilis* chromosomal DNA was amplified using either an exonuclease-resistant standard random hexamer primer sequence, NNNN*N*N or using an exonuclease-resistant random hexamer primer sequence, SP2-NNNNN*N (structure IV), wherein an oligocation moiety (SP2) comprising a dimeric spermine moiety was covalently conjugated to the 5' terminal end of a sequence, NNNNN*N to determine relative amplification levels at four different bacterial loci. Overall amplification level was about 25 million fold. 10 ng of this amplified libraries from each of the amplification reaction were then analyzed using standard SYBR Green-1 based quantitative PCR (qPCR) using specific primer sets targeting four different genomic loci (LytD, YdcQ, DnaK, and MenF) to sample effectiveness of oligocation-oligonucleotide conjugate primers for promoting sensitive and balanced DNA amplification. Reactions were performed in triplicate and the absolute Ct values of these four genomic loci in each of the amplicon libraries were compared with the values from unamplified bacterial DNA to determine the relative representation levels. FIG. 2 illustrates the data plotted as a log 2 ratio where a value of 0 indicates equal representation of the loci compared to the unamplified bacterial DNA control. As depicted in FIG. 2, the oligocation-oligonucleotide conjugate primer, SP2-NNNNN*N, illustrated better sequence coverage and amplification balance compared to the random primer, NNNN*N*N. The products amplified using the spermine-modified hexamer retained relatively even coverage of the four loci, whereas the products amplified from the standard hexamer displayed under-amplification and loss of some sequence.

Example 3

Amplification of DNA from Single Bacterial Cells Using Spermine-Modified Random Hexamer Primer

Figure 3:
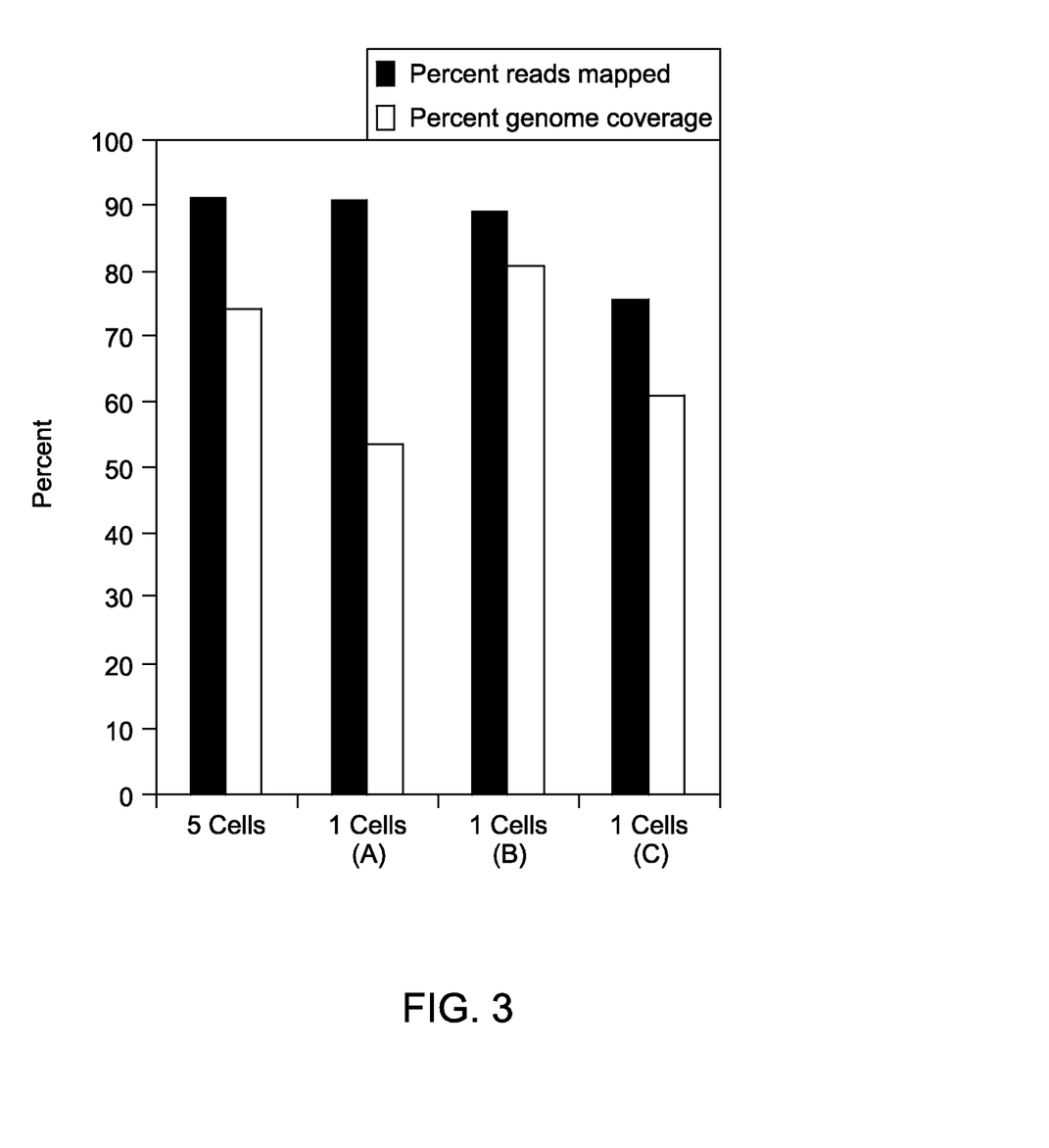
FIG. 3 illustrates amplification of DNA from a single bacterial cell using a spermine-modified random hexamer primer.

*E. coli* cells were isolated by dilution, stained with FM 1-43 FX membrane dye (Molecular Probes), and counted using an inverted fluorescence microscope. Cells were lysed by addition of an equal volume of lysis buffer (0.4 M KOH, 100 mM DTT, 0.02% Tween-20), incubated for 5 minutes, and neutralized with one volume of neutralization buffer (0.4M HCl, 0.6M Tris, pH 7.5). MDA reactions utilizing the spermine-modified hexamers were performed with 1 to 5 isolated *Escherichia coli* cells. Reactions (20 µL) contained 50 mM HEPES, pH 8.0, 20 mM $MgCl_2$, 0.01% Tween-20, 1 mM TCEP, 2.5% PEG-8000, 15 µM SP2-NNNNN*N, 20 µg/ml Phi29 polymerase, SYBR Green I dye (Invitrogen) at 1:20,000 dilution, and 3 µL of the *E. coli* lysate. Incubation was at 30° C. for 5 hours. Total amplification in the single cell reactions was approximately 400,000,000-fold. Amplified DNA was processed into libraries and subjected to Illumina GA (Illumina, San Diego, Calif.) whole-genome sequencing with a 100 nucleotide read length. Eight (8) million reads for each sample were mapped to the *E. coli* reference genome and the percent of reads that mapped and the percent of the genome coverage with at least one overlapping read were determined MDA reaction utilizing spermine-modified random hexamers was robust and sensitive enough to allow for the amplification of DNA from a few and even single bacterial cells. As depicted in FIG. 3, more than about 75% (75-90%) of the reads were mapped to the *E. coli* reference genome upon amplification of DNA from a single cell of bacterium. Further, the read represented more than about 53% (53-80%) of the genome upon single cell DNA amplification using spermine-modified random hexamer primers.

The above detailed description is exemplary and not intended to limit the invention of the application and uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the invention. At the very least, and not as an attempt to limit the application of the doctrine of equivalents to the scope of the claims, each numerical parameter should at least be construed in light of the number of reported significant digits and by applying ordinary rounding techniques. Where necessary, ranges have been supplied, and those ranges are inclusive of all sub-ranges there between.

The invention may be embodied in other specific forms without departing from the spirit or essential characteristics thereof. The foregoing embodiments are selected embodiments or examples from a manifold of all possible embodiments or examples. The foregoing embodiments are therefore to be considered in all respects as illustrative rather than limiting on the invention. While only certain features of the invention have been illustrated and described herein, it is to be understood that one skilled in the art, given the benefit of this disclosure, will be able to identify, select, optimize or modify suitable conditions/parameters for using the methods in accordance with the principles of the invention, suitable for these and other types of applications. The precise use, choice of reagents, choice of variables such as concentration, volume, incubation time, incubation temperature, and the like may depend in large part on the particular application for which it is intended. It is, therefore, to be understood that the appended claims are intended to cover all modifications and changes that fall within the spirit of the invention. Further, all changes that come within the meaning and range of equivalency of the claims are intended to be embraced therein.

The invention claimed is:

1. A method for producing at least one amplicon based on a target DNA, the method comprising:
    (a) providing the target DNA;
    (b) providing a DNA amplification reaction mixture comprising an oligocation-oligonucleotide conjugate primer, a DNA polymerase having a strand displacement activity, and a dNTP mixture; and
    (c) amplifying at least one portion of the target DNA using the DNA amplification reaction mixture of step (b) to produce the at least one amplicon,
    wherein the oligocation-oligonucleotide conjugate primer comprises an oligocation moiety covalently conjugated to the 5' end of an oligonucleotide sequence wherein the oligocation moiety comprises at least one lysine moiety, and
    wherein the amplification is performed under isothermal conditions.

2. The method of claim 1, wherein the oligocation moiety is a cationic polyamine.

3. The method of claim 2, wherein the oligonucleotide sequence is a random oligonucleotide sequence or a partially constrained oligonucleotide sequence.

4. The method of claim 3, wherein the oligonucleotide sequence comprises a nucleotide analogue.

5. The method of claim 3, wherein the oligonucleotide sequence comprises a phosphorothioate linkage between a 3' terminal nucleotide and a nucleotide that is adjacent to the 3' terminal nucleotide.

6. The method of claim 5, wherein the oligonucleotide sequence is NNNNN*N.

7. A method of producing at least one amplicon based on a target DNA comprising:
    providing the target DNA;
    annealing at least one oligocation-oligonucleotide conjugate primer to the target DNA to generate a target DNA: primer hybrid; and
    extending the oligocation-oligonucleotide conjugate primer in the target DNA:primer hybrid via an isothermal nucleic acid amplification reaction to produce the at least one amplicon complementary to at least one portion of the target DNA,
    wherein the oligocation-oligonucleotide conjugate primer comprises an oligocation moiety covalently conjugated to the 5' end of an oligonucleotide sequence and wherein the oligocation moiety comprises at least one lysine moiety.

8. The method claim 7, wherein the isothermal nucleic acid amplification is multiple strand displacement nucleic acid amplification or rolling circle amplification.

9. The method of claim 7, wherein the oligocation-oligonucleotide conjugate primer comprises a random pentamer sequence or a random hexamer sequence.

* * * * *